United States Patent
Chen (10) Patent No.: US 10,814,023 B2
(45) Date of Patent: Oct. 27, 2020

(54) ELECTROCHEMICAL PAPER TOWEL STERILIZING DEVICE

(71) Applicant: Chien-Hung Chen, New Taipei (TW)

(72) Inventor: Chien-Hung Chen, New Taipei (TW)

( * ) Notice: Subject to any disclaimer, the term of this patent is extended or adjusted under 35 U.S.C. 154(b) by 0 days.

(21) Appl. No.: 16/143,480

(22) Filed: Sep. 27, 2018

(65) Prior Publication Data

US 2020/0101181 A1 Apr. 2, 2020

(51) Int. Cl.
*A61L 2/00* (2006.01)
*A61L 2/20* (2006.01)
*C02F 1/467* (2006.01)
*A61L 2/18* (2006.01)
*C25B 1/26* (2006.01)

(52) U.S. Cl.
CPC .............. *A61L 2/0088* (2013.01); *A61L 2/208* (2013.01); *C02F 1/467* (2013.01); *A61L 2/186* (2013.01); *C25B 1/26* (2013.01)

(58) Field of Classification Search
CPC ........ A61L 2/0088; A61L 2/208; A61L 2/186; C02F 1/467; C25B 1/26
See application file for complete search history.

(56) References Cited

U.S. PATENT DOCUMENTS

| | | | | |
|---|---|---|---|---|
| 6,387,238 B1 * | 5/2002 | Merk | ...................... | A01N 37/16 204/252 |
| 2006/0219261 A1 * | 10/2006 | Lin | ..................... | A61B 1/00057 134/18 |
| 2007/0207074 A1 * | 9/2007 | Jethrow | ..................... | A61L 2/04 422/292 |
| 2008/0255498 A1 * | 10/2008 | Houle | .................... | A61C 17/02 604/20 |
| 2013/0152982 A1 * | 6/2013 | Tanaka | ................... | A61B 1/123 134/115 R |
| 2014/0131217 A1 * | 5/2014 | Buschmann | .............. | C01B 7/01 205/440 |
| 2017/0057847 A1 * | 3/2017 | Huang | .................. | C02F 1/4672 |

* cited by examiner

*Primary Examiner* — Sean E Conley
*Assistant Examiner* — Brendan A Hensel
(74) *Attorney, Agent, or Firm* — Leong C. Lei (57) ABSTRACT

The present invention is related to an electrochemical paper towel sterilizing device, which mainly comprises: at least one sterilizing device, at least one first accommodating space, at least one water-inlet portion, at least one electrolytic component, at least one power-supply element, and at least one second accommodating space. In this way, the second accommodating space is provided with a dry wiping-object (such as a paper towel), and the user can add water into the first accommodating space via the water-inlet portion and electrolyze the water through the electrolytic component to generate the high active oxygen species, and combine the water and the high active oxygen species into the wiping-object, thereby producing a wet wiping-object with sterilizing effect.

6 Claims, 9 Drawing Sheets

ELECTROCHEMICAL PAPER TOWEL STERILIZING DEVICE

(a) TECHNICAL FIELD OF THE INVENTION

The present invention provides an electrochemical paper towel sterilizing device for producing a wet wiping-object with sterilizing effect by electrolyzing water to produce the high active oxygen species.

(b) DESCRIPTION OF THE PRIOR ART

For example, the "sterilization paper towel" of the Republic of China Patent Notice No. M471843 which technical content mainly includes: "A sterilizing paper towel, which mainly has a paper towel and a packaging bag, wherein the paper towel can be a liquid-absorbent carrier such as a dust-free paper, a Spunlace Nonwoven, or a microfiber cloth . . . , etc. And, the paper towel of this invention is further infiltrated by a sterilizing liquid and then contained in a packaging bag, wherein the sterilizing liquid contains a chlorine dioxide component to have the reactive and oxidizing ability. Moreover, the sterilizing liquid has a reactive compound, so the sterilizing liquid will decompose rapidly without residue in the natural environment and will not cause a secondary pollution. The sterilizing liquid is harmless to humans and animals for a general application concentration, and the sterilizing liquid has many advantages, for example, there is no need to have an isolation and clearance space during the sterilization. Therefore, the paper towel does not cause harm to the human body when using. And, the paper towel is wrapped in the packaging bag after absorbing the sterilizing liquid; so that the packaging bag can moisturize the paper towel under normal conditions, therefore the paper towel is convenient for the user to carry and use.

However, although the sterilizing liquid has the sterilizing function, the paper towel is stored in the packaging bag; so that the used packaging bag will become garbage; and the paper towel can be made of a dust-free paper, a Spunlace Nonwoven, or a microfiber cloth . . . , etc. which are not easily decomposed by the environment and so as to impose a burden on the environment; and the user himself cannot make a paper towel having a sterilization function.

SUMMARY OF THE INVENTION

The main purposes of the present invention is to electrolyze the water in the first accommodating space through the electrochemical system and components, thereby generating the high active oxygen species with bactericidal effect in the water; and using the design of joining first accommodating space to the second accommodating space, so that the water with high active oxygen species can be integrated with the wiping-object to produce a wet wiping-object with sterilizing effect.

The main structure of the present invention for achieving the above objects comprises at least one sterilizing device and one space for integrating water and wiping-object. The sterilizing device defines at least one first accommodating space for accommodating water, and at least one water-inlet portion that communicates with the first accommodating space. And, the first accommodating space is set with at least one electrolytic component which is supplied to electrolyze water to generate the high active oxygen species for sterilizing And, the sterilizing device is set with at least one power-supply element electrically connected with the electrolytic component. Further, at least one second accommodating space that communicates with the first accommodating space is configured to accommodate at least one wiping-object. In this way, the user can place a dry wiping-object in the second accommodating space and inject water into the first accommodating space via the water-inlet portion.

The electrolytic component can be used to electrolyze the water to produce a high active oxygen species with sterilizing effect; and the first accommodating space is connected to the second accommodating space, so that the water with high active oxygen species can be integrated with the wiping-object to produce a wet wiping-object with sterilizing effect.

DETAILED DESCRIPTION OF THE PREFERRED EMBODIMENTS

The following descriptions are exemplary embodiments only, and are not intended to limit the scope, applicability or configuration of the invention in any way. Rather, the following detailed description provides a convenient illustration for implementing exemplary embodiments of the invention. Various changes to the described embodiments may be made in the function and arrangement of the elements described without departing from the scope of the invention as set forth in the appended claims.

The foregoing and other aspects, features, and utilities of the present invention will be best understood from the following detailed description of the preferred embodiments when read in conjunction with the accompanying drawings.

Figure 1:
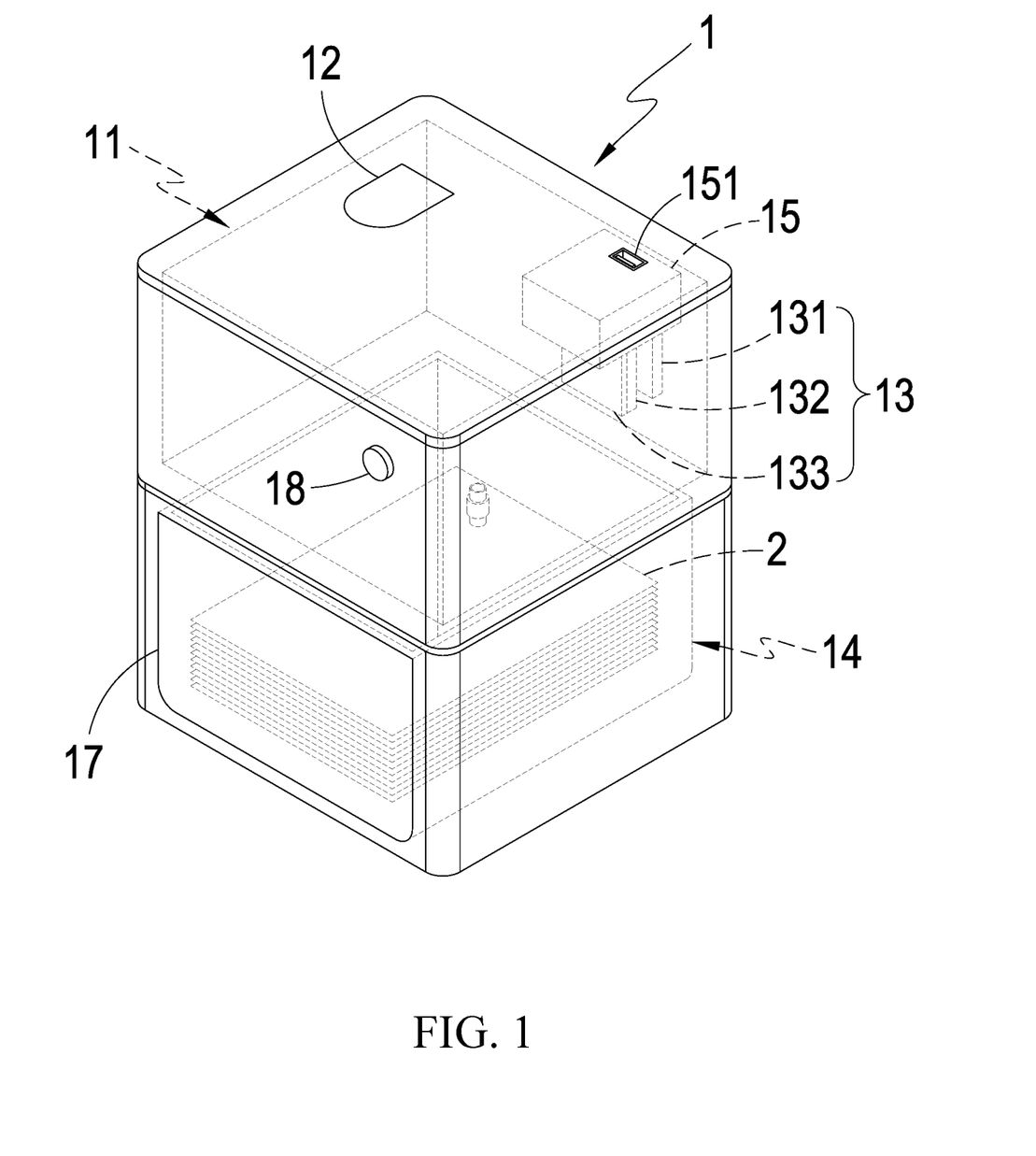
FIG. 1 is a perspective view of a preferred embodiment of the present invention.
Figure 2:
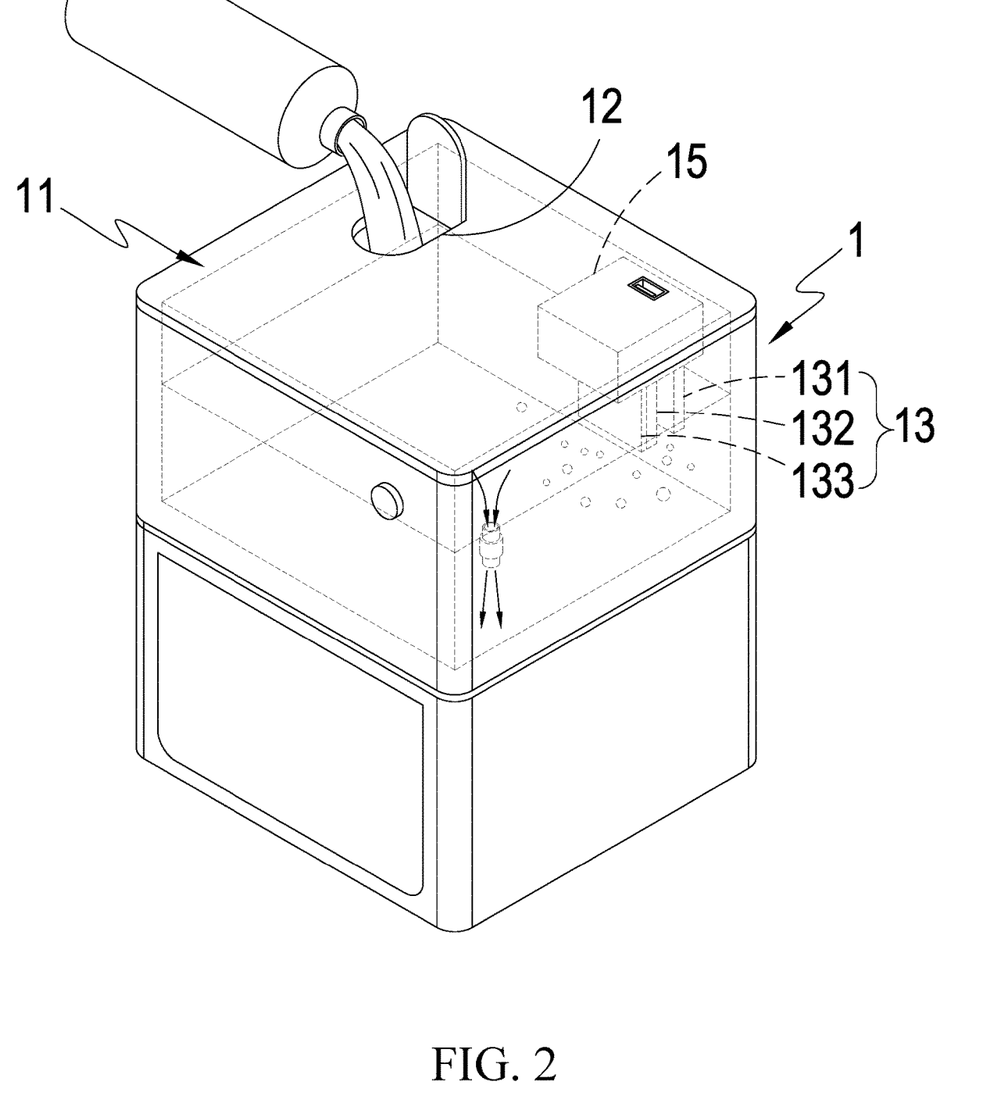
FIG. 2 is an implementation schematic diagram 1 of the preferred embodiment of the present invention.

As shown in FIG. 1, this embodiment of the present invention comprises: at least one sterilizing device 1 having at least one first accommodating space 11 for accommodating water, and the sterilizing device 1 defining at least one water inlet portion 12 communicating with the first accommodating space 11; wherein this embodiment has a cover for selectively closing the first accommodating space 11; at least one electrolytic component 13 set in the first accommodating space 11 is configured to supply water to generate high active oxygen species for sterilization; wherein the electrolytic component 13 comprises at least one anode element 131, at least one cathode element 132 set at the side of the anode element 131, and at least one carbon material 133 set on the cathode element 132; at least one power-supply element 15 set on the sterilizing device 1 and electrically connected with the electrolytic component 13; wherein at least one electricity-charging portion 151 electrically connected with the power-supply element 15 is set on the sterilizing device, and the electricity-charging portion 151 is a Universal Serial Bus (USB) charging socket; at least one shell-body 17 is movably set on the sterilizing device 1, wherein the shell-body 17 defines at least one second accommodating space 14, and the second accommodating space 14 communicated with the first accommodating space 11 is for accommodating at least one wiping-object 2 (such as a paper towel, a non-woven fabric, a cloth) and for combing the water and the high active oxygen species to the wiping-object 2; and at least one water-injection element 18 is set on the sterilizing device 1 for controlling the first accommodating space 11 to selectively communicate with the second accommodating space 14.

As shown in FIG. 1 to FIG. 4, the shell-body 17 is made of a silicone material in the present embodiment, which the shell-body 17 is detachably mounted on the sterilizing device 1 and the user can place a dry wiping-object 2 in the accommodating space 14 of the shell-body 17. When the user needs to make a wet wiping-object 2, the water can be injected into the first accommodating space 11 from the water-inlet portion 12 on the sterilizing device 1, and the water is electrolyzed by the electrolytic component 13 to produce a high active oxygen species with a sterilizing effect. The electrolytic component 13 comprises an anode element 131 and a cathode element 132 respectively connected with the anode and the cathode of the power-supply element 15; wherein the cathode element 132 has a carbon material 133 on it, and the anode element 131 and the cathode element 132 are both in contact with water; therefore the power-supply element 15 can supply electric energy to drive the electrolytic component 13 to electrolyze the water to generate the high active oxygen species in the water. And, the high active oxygen species is one of a superoxide anion ($O_2$—.), a hydroxyl radical (.OH), a hydrogen peroxide ($H_2O_2$), or a single oxygen ($^1O_2$) which has a sterilizing effect. And, the power-supply element 15 is a rechargeable battery, and the user can charge the power-supply element 15 by using the electricity-charging portion 151. The electricity-charging portion 151 of this embodiment is exemplified by a Universal Serial Bus (USB) charging socket, which the power-supply element 15 can also be a mains-supply.

Figure 3:
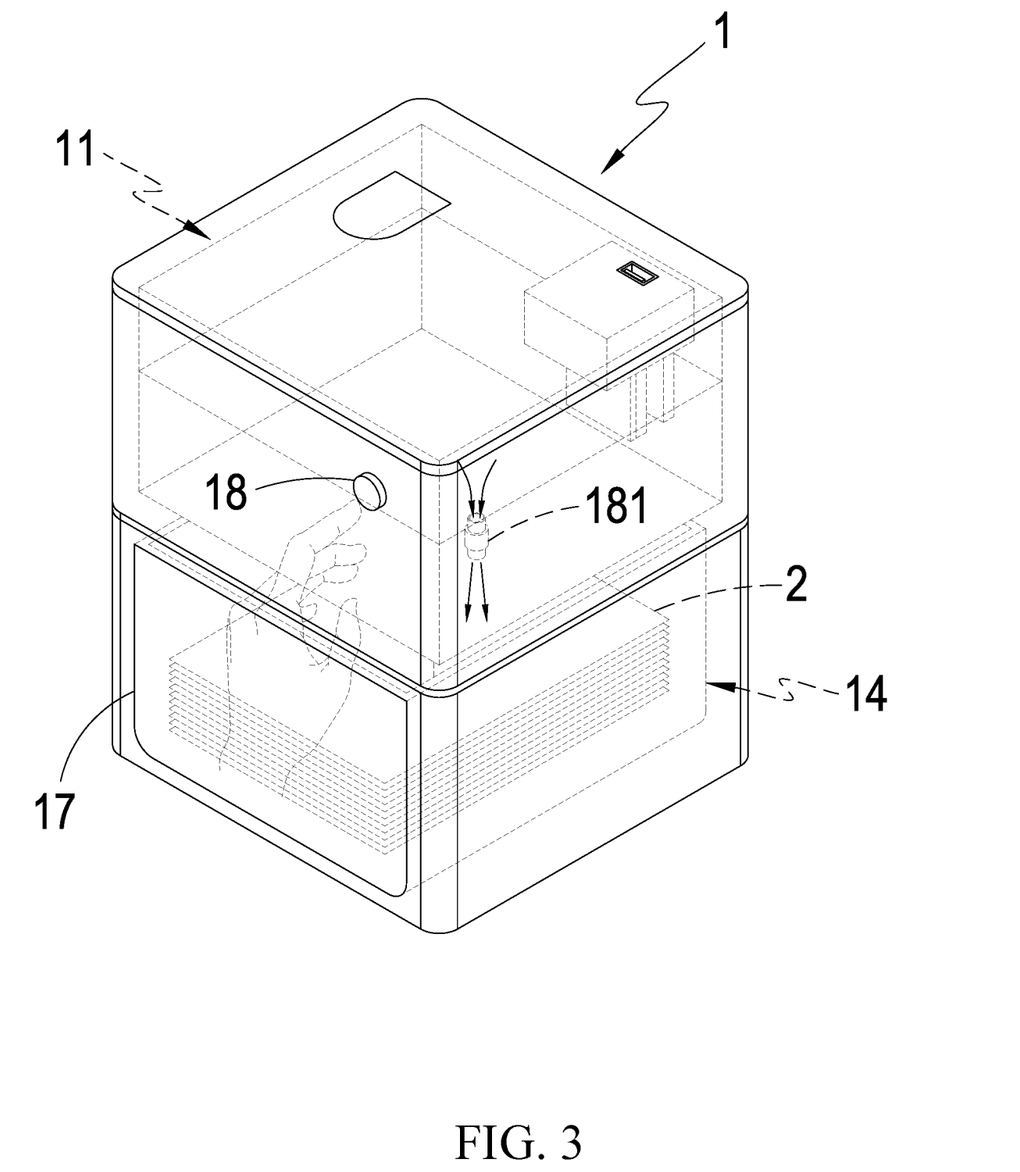
FIG. 3 is an implementation schematic diagram 2 of the preferred embodiment of the present invention.
Figure 4:
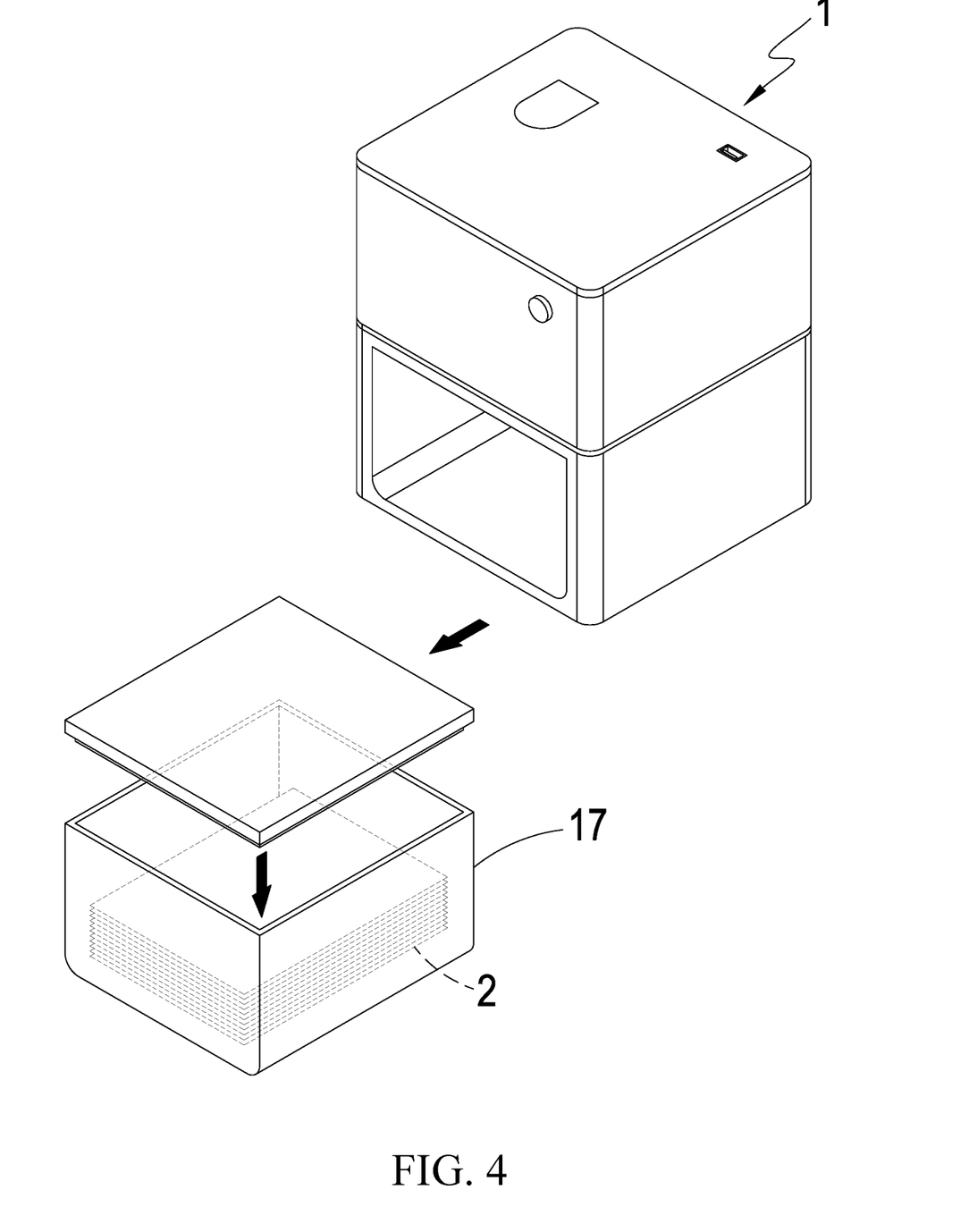
FIG. 4 is an implementation schematic diagram 3 of the preferred embodiment of the present invention.

As shown in FIG. 3 to FIG. 4, the user can press the water-injection element 18 to linkingly open the electronic-valve 181 between the first accommodating space 11 and the second accommodating space 14 to combine the water and the high active oxygen species with the dry wiping-object 2 to produce a wet wiping-object 2 having the sterilizing effect, and the user can also remove the shell-body 17 from the sterilizing device 1 and attach a cover on the shell-body 17 to facilitate carrying the wet wiping-object 2 with him.

Figure 5:
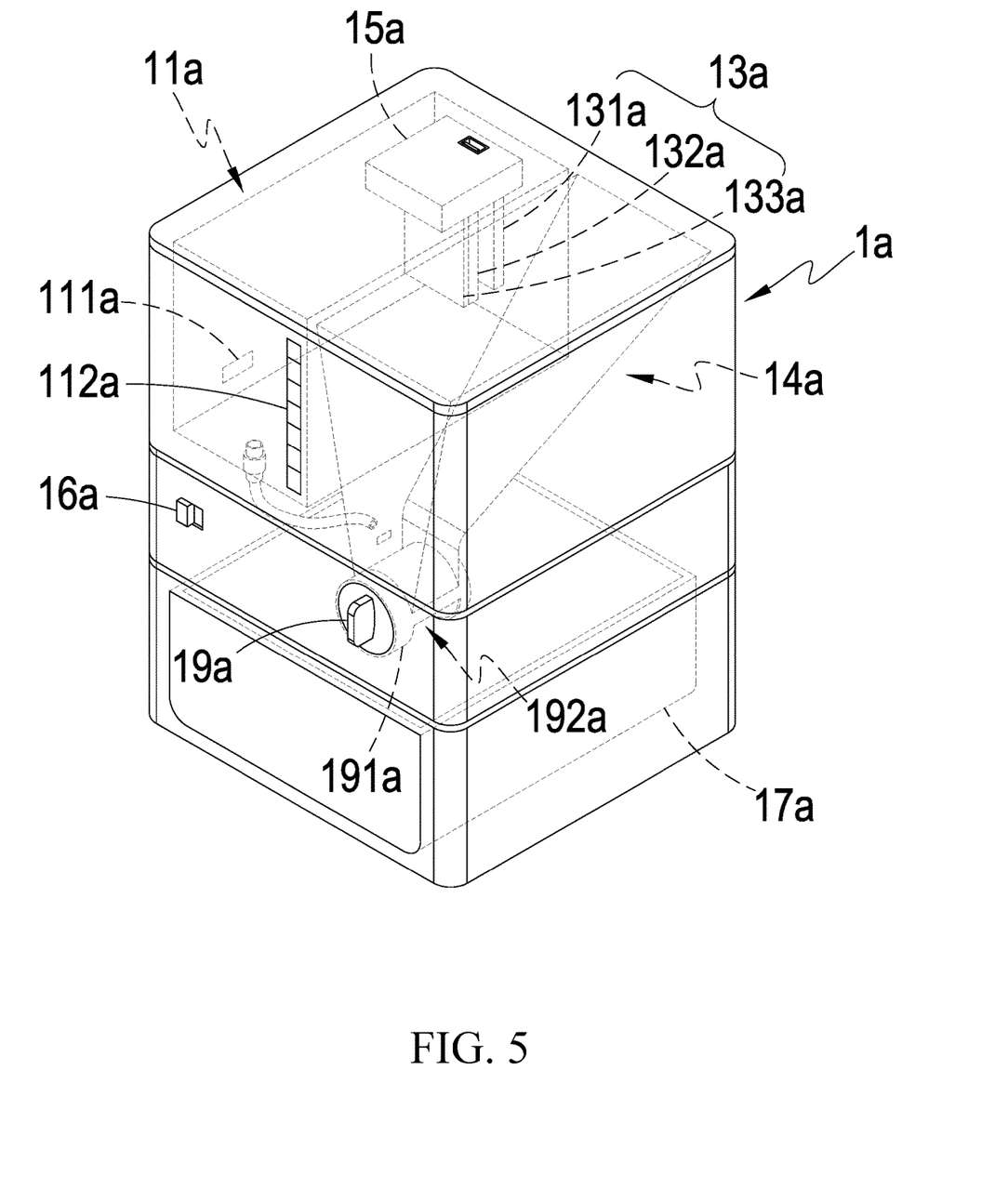
FIG. 5 is a perspective view of another preferred embodiment of the present invention.

As shown in FIG. 5, this embodiment of the present invention comprises: at least one sterilizing device 1a having at least one first accommodating space 11a for accommodating water; at least one electrolytic component 13a set in the first accommodating space 11a is configured to supply water to generate high active oxygen species for sterilization; wherein the electrolytic component 13a comprises at least one anode element 131a, at least one cathode element 132a set at the side of the anode element 131a, and at least one carbon material 133a set on the cathode element 132a; at least one power-supply element 15a set on the sterilizing device 1a and electrically connected with the electrolytic component 13a; wherein the sterilizing device 1a is set with at least one switching element 16a electrically connected to the power-supply element 15a; at least one water-level-detecting element 111a set in the first accommodating space 11a, and the sterilizing device 1a is set with at least one water-level-display element 112a electrically connected with the water-level-detecting element 111a; at least one second accommodating space 14a communicated with the first accommodating space 11a is for accommodating at least one wiping-object and for combing the water and the high active oxygen species to the wiping-object; and at least one shell-body 17a movably set on the sterilizing device 1a, wherein the second accommodating space 14a communicates with the shell-body 17a, and the sterilizing device 1a is set with a control element 19a for controlling the second accommodating space 14a to selectively connect with the shell-body 17a; and the control element 19a comprises a rotation seat 191a set between the second accommodating space 14a and the shell-body 17a, wherein the rotation seat 191a has at least one temporary-storing opening 192a selectively communicating with the second accommodating space 14a or the shell-body 17a.

As shown in FIG. 5 to FIG. 9, the sterilizing device 1 of the present embodiment is in the form of a capsule-toy machine. The user can inject water into the first accommodating space 11a of the sterilizing device 1a, which the water-level-detecting element 111a can detect the water-level inside of the first accommodating space 11a and the water-level-display element 112a displays the water-level in the first accommodating space 11a. Furthermore, the power-supply element 15a can supply electric energy to the electrolytic component 13a, and the electrolytic component 13a has a switching element 16a that controls the electrolytic component 13a to electrolyze the water. When the switching element 16a is turned on, the anode element 131a, the cathode element 132a, and the carbon material 133a in the electrolytic component 13a can electrolyze the water to produce a high active oxygen species, such as a superoxide anion ($O_2$—.), a hydroxyl radical (.OH), a hydrogen peroxide ($H_2O_2$), or a single oxygen ($^1O_2$).

Figure 6:
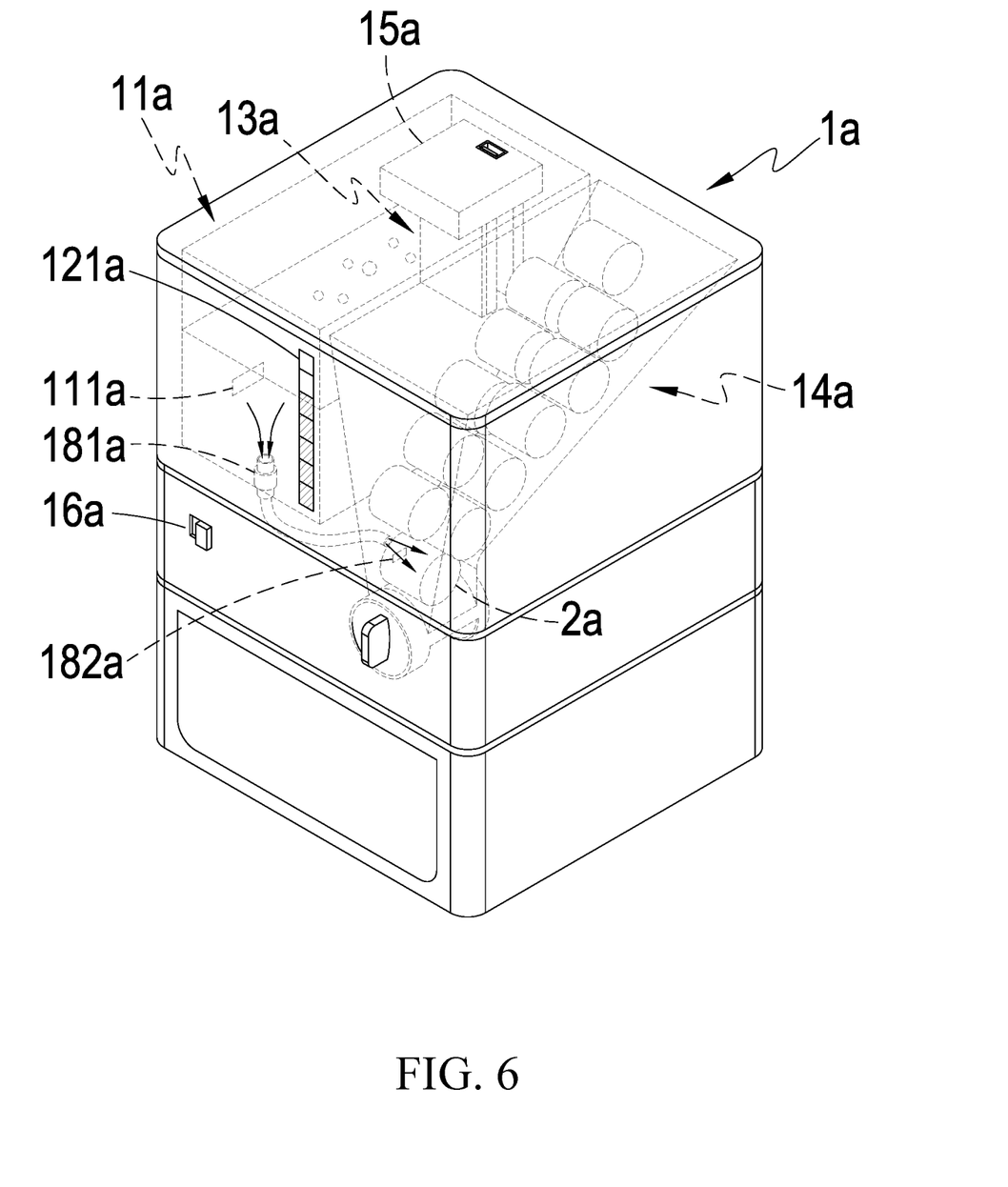
FIG. 6 is an action schematic diagram 1 of another preferred embodiment of the present invention.
Figure 7:
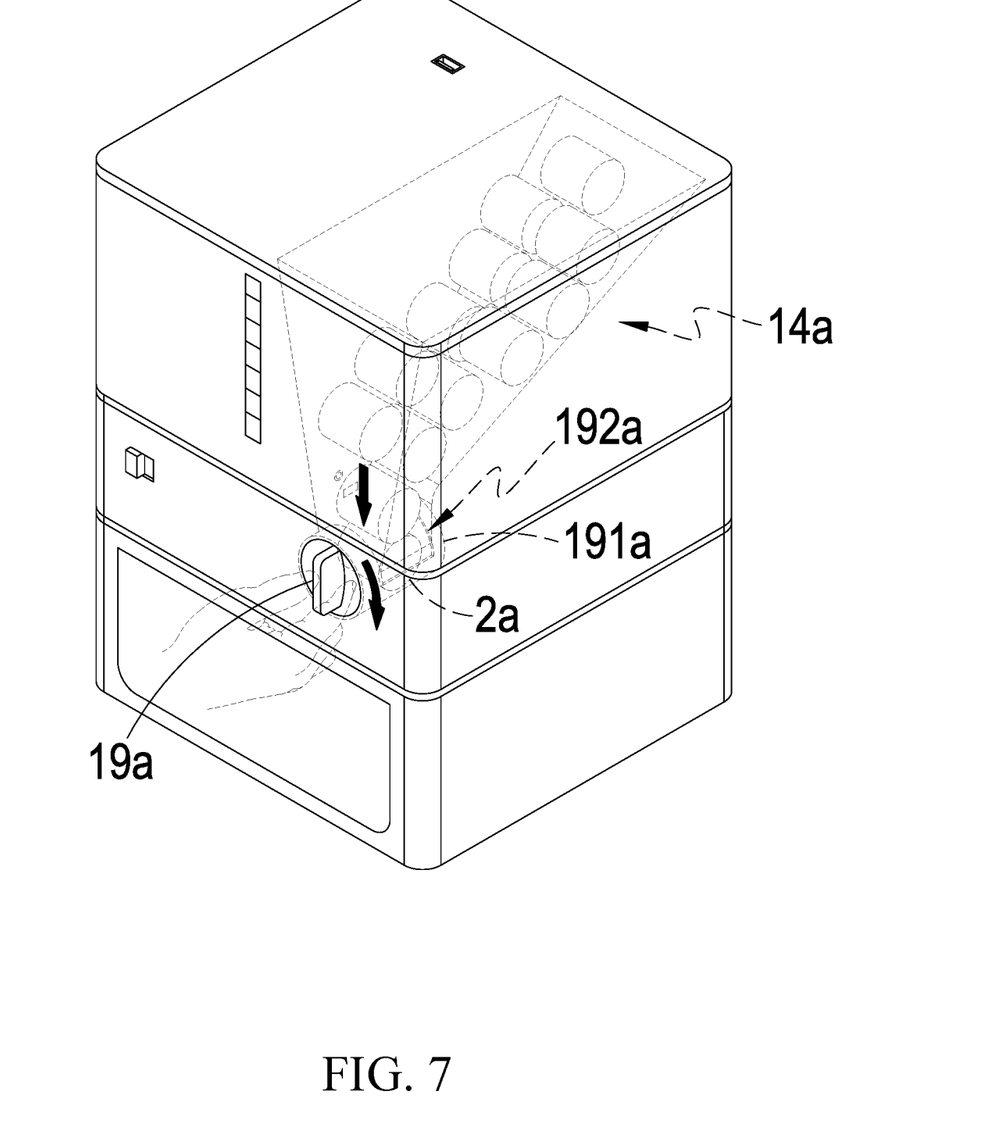
FIG. 7 is an action schematic diagram 2 of another preferred embodiment of the present invention.
Figure 8:
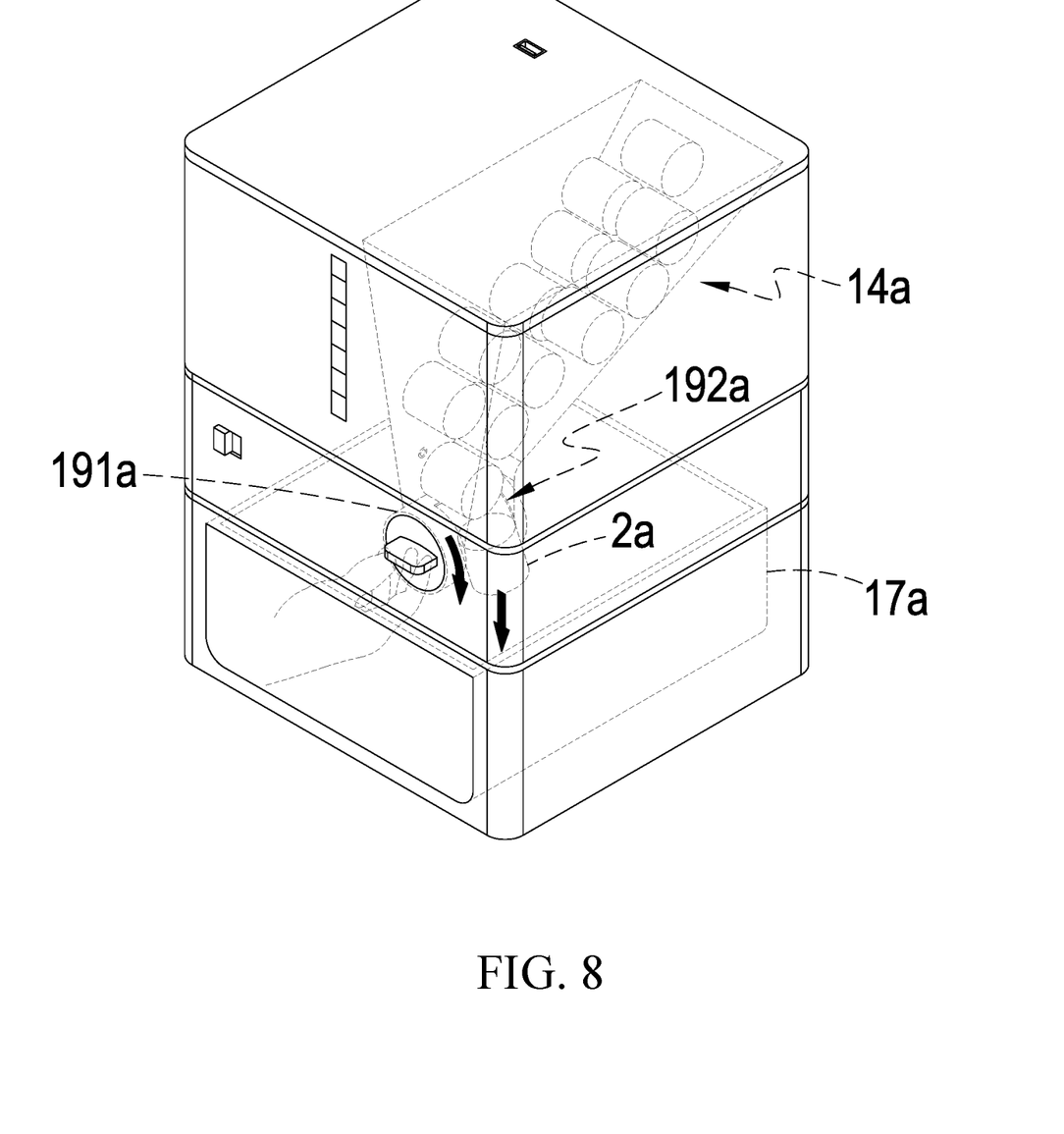
FIG. 8 is an action schematic diagram 3 of another preferred embodiment of the present invention.
Figure 9:
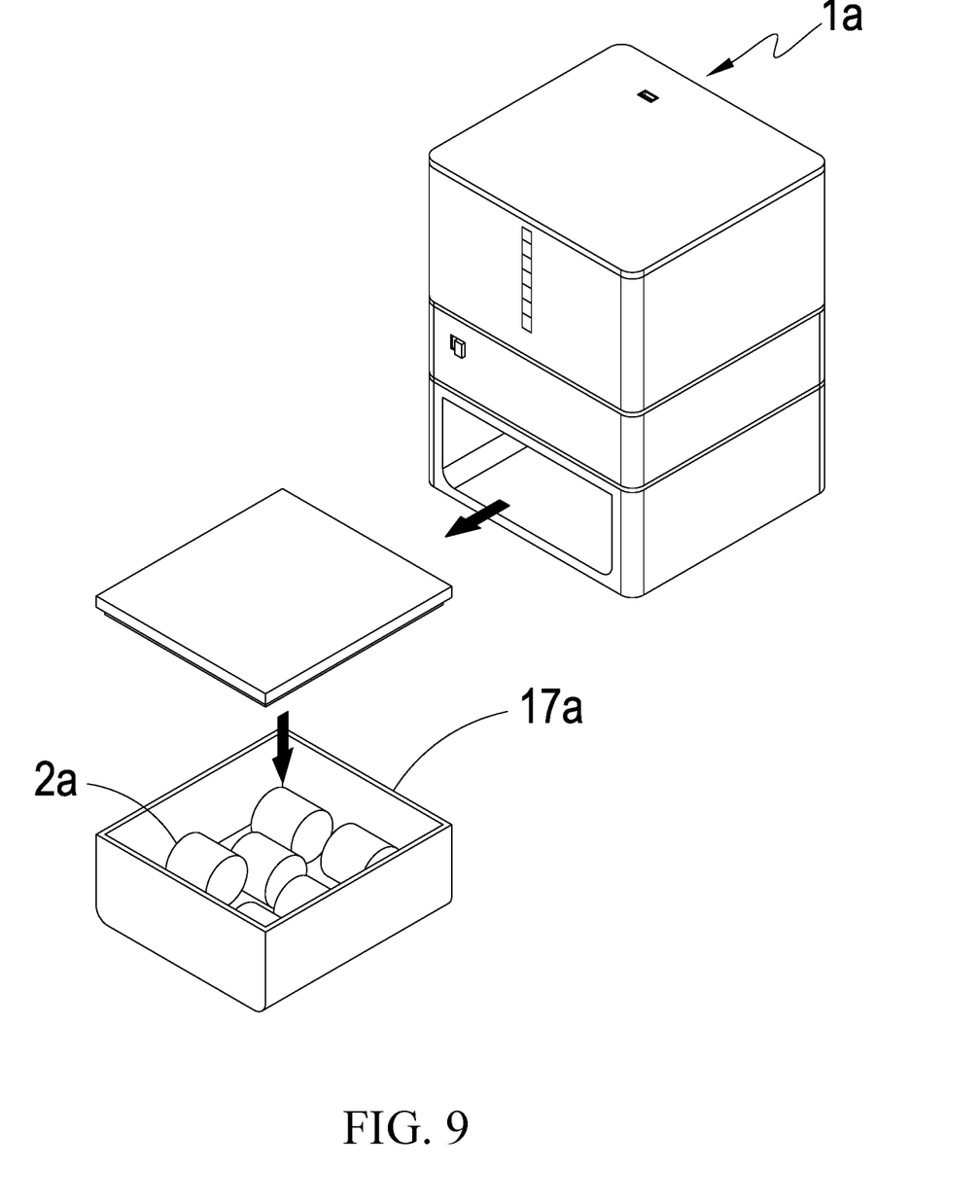
FIG. 9 is an implementation schematic diagram of one more preferred embodiment of the present invention.

As shown in FIG. 6, in this embodiment, the second accommodating space 14a is in the form of a funnel, and a cylindrical dry wiping-object 2a is placed inside, which an infrared sensor 182a is also matched inside. When the presence of the wiping-object 2a is detected, the electronic-valve 181a is controlled to flow a certain amount of water with high active oxygen species to the narrow opening of the second accommodating space 14a to wet the wiping-object 2a. When the user needs to use the wet wiping-object 2a, as shown in FIG. 7, the control element 19a of a rotatable knob form can be rotated by the interlocking rotary seat 191a, which the temporary-storing opening 192a of the rotation seat 191a is connected to the second upper portion of the second accommodating the space 14a, and it will cause a wiping-object 2a to fall into the temporary-storing opening 192a. Then, rotating the control element 19a again, as shown in FIG. 8, the temporary-storing opening 192a is brought into communication with the lower shell-body 17a, and the second accommodation space 14a is blocked by the bottom of the rotation seat 191a, so that the wiped object 2a is dropped into the shell-body 17a via the temporary-storing opening 192a. Thereby, the user can obtain the wet wiping-object 2a by using the operation principle similar to the capsule-toy machine, and the user can remove the shell-body 17a from the sterilizing device 1a and attach a cover on the casing 17a to facilitate carrying the wet wiping-object 2a with him.

Therefore, when using the present invention, compared with the conventional technology, the following advantages exist:
1. Through the design of the electrolytic component 13 and the first accommodating space 11, the water in the first accommodating space 11 can be electrolyzed to produce a high active oxygen species having bactericidal effect.
2. Through the design of the first accommodating space 11 communicating with the second accommodating space 14, the water with high active oxygen species can be integrated to the wiping-object 2 to produce a wet wiping-object 2 having a sterilizing effect.
3. Through the design that the housing 17 can be removed from the sterilizing device 1, it can allow the user to conveniently carry the wet wiping-object 2 with him.
4. Through the design of the sterilizing device 1*a* is in the form of a capsule-toy machine, it can allow the user to increase the fun in use.

I claim:

1. An electrochemical paper towel sterilizing device, which comprises:
    at least one sterilizing device;
    at least one first accommodating space defined in the sterilizing device for accommodating water;
    at least one water-inlet portion defined on the sterilizing device and communicated with the first accommodating space;
    at least one electrolytic component set in the first accommodating space and comprising at least one anode element, at least one cathode element spaced from the anode element, and at least one carbon material attached to the cathode element, wherein the electrolytic component is operable to electrolyze the water to generate active oxygen species for sterilization, the active oxygen species being mixed in the water;
    at least one power-supply element set on the sterilizing device and electrically connected with the electrolytic component; and
    at least one second accommodating space connected with the first accommodating space, wherein the second accommodating space receives and holds therein at least one wiping-object and wherein the water mixed with the active oxygen species is selectively conducted from the first accommodating space into the second accommodating space to allow the active oxygen species mixed in the water to contact and combine with the wiping-object,
    wherein the sterilizing device is movably set with at least one shell-body;
    wherein the second accommodating space is connected to the shell-body, and the sterilizing device is set with a control element for controlling the second accommodating space to selectively communicate with the shell-body; and
    wherein a rotation seat is linkingly set on one side of the control element and set between the second accommodating space and the shell-body, and the rotation seat has at least one temporary-storing opening selectively communicating with the second accommodating space or the shell-body.

2. The electrochemical paper towel sterilizing device according to claim 1, wherein the first accommodating space is set with at least one water-level-detecting element, and the sterilizing device is set with at least one water-level-display element electrically connected with the water-level-detecting element.

3. The electrochemical paper towel sterilizing device according to claim 1, wherein the sterilizing device is provided with at least one switching element electrically connected with the power-supply element.

4. The electrochemical paper towel sterilizing device according to claim 1, wherein the sterilizing device is set with at least one electricity-charging portion electrically connected to the power-supply element.

5. The electrochemical paper towel sterilizing device according to claim 4, wherein the electricity-charging portion is a Universal Serial Bus (USB) charging socket.

6. The electrochemical paper towel sterilizing device according to claim 1, wherein the second accommodating space is defined in the shell-body, and the sterilizing device is set with a water-injection element for controlling the first accommodating space to selectively communicate with the second accommodating space.

\* \* \* \* \*